(12) United States Patent
Tang et al.

(10) Patent No.: US 11,471,045 B2
(45) Date of Patent: Oct. 18, 2022

(54) DIAGNOSTIC CLASSIFICATION OF CORNEAL SHAPE ABNORMALITIES

(71) Applicant: Oregon Health & Science University, Portland, OR (US)

(72) Inventors: Maolong Tang, Portland, OR (US); Yan Li, Portland, OR (US); David Huang, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 417 days.

(21) Appl. No.: 16/547,110

(22) Filed: Aug. 21, 2019

(65) Prior Publication Data

US 2020/0054208 A1    Feb. 20, 2020

Related U.S. Application Data

(63) Continuation of application No. 15/639,842, filed on Jun. 30, 2017, now abandoned.
(Continued)

(51) Int. Cl.
*G06K 9/00* (2022.01)
*A61B 3/107* (2006.01)
(Continued)

(52) U.S. Cl.
CPC .......... *A61B 3/107* (2013.01); *A61B 3/0025* (2013.01); *A61B 3/1005* (2013.01);
(Continued)

(58) Field of Classification Search
CPC ..... A61B 3/107; A61B 3/0025; A61B 3/1005; A61B 3/102; G06T 7/62; G06T 7/0014;
(Continued)

(56) References Cited

U.S. PATENT DOCUMENTS

| 8,690,328 B1* | 4/2014 | Chong | .................. A61B 3/102 |
| | | | 351/205 |
| 9,655,512 B2* | 5/2017 | Huang | ................. A61B 3/1005 |

(Continued)

OTHER PUBLICATIONS

Tang, Maolong, et al. "Differentiating keratoconus and corneal warpage by analyzing focal change patterns in corneal topography, pachymetry, and epithelial thickness maps." Investigative ophthalmology & visual science 57.9 (2016): OCT544-OCT549.
(Continued)

*Primary Examiner* — Avinash Yentrapati
(74) *Attorney, Agent, or Firm* — Schwabe, Williamson & Wyatt, P.C.

(57) ABSTRACT

Disclosed are systems and methods for characterizing corneal shape abnormalities. These methods may be used to differentiate corneas having subclinical keratoconus from other conditions which cause distortion of corneal shape, including warpage of the cornea due to contact lens wear. Also disclosed is classification scheme to aid diagnosis of corneal conditions and thereby guide clinical decision making regarding patient treatment. This classification scheme is based on computed properties of corneal shape, is amenable to automation, and may be implemented in an integrated system or provided in the form of software encoded on a computer-readable medium.

34 Claims, 11 Drawing Sheets

Related U.S. Application Data

(60) Provisional application No. 62/357,198, filed on Jun. 30, 2016.

(51) Int. Cl.
*A61B 3/00* (2006.01)
*G06K 9/62* (2022.01)
*G06T 7/60* (2017.01)
*G06T 7/00* (2017.01)
*G06T 7/62* (2017.01)
*A61B 3/10* (2006.01)

(52) U.S. Cl.
CPC .......... *G06K 9/6267* (2013.01); *G06T 7/0014* (2013.01); *G06T 7/0016* (2013.01); *G06T 7/60* (2013.01); *G06T 7/62* (2017.01); *A61B 3/102* (2013.01); *G06T 2207/10101* (2013.01); *G06T 2207/30041* (2013.01)

(58) Field of Classification Search
CPC ..................... G06T 7/0016; G06T 7/60; G06T 2207/10101; G06T 2207/30041; G06K 9/6267

See application file for complete search history.

(56) References Cited

U.S. PATENT DOCUMENTS

| | | | | |
|---|---|---|---|---|
| 2004/0233387 | A1* | 11/2004 | Huang | A61F 9/008 351/212 |
| 2006/0187413 | A1* | 8/2006 | Applegate | A61B 3/0025 351/246 |
| 2007/0282313 | A1* | 12/2007 | Huang | A61F 9/00831 606/5 |
| 2007/0291228 | A1* | 12/2007 | Huang | A61B 3/107 703/2 |
| 2008/0309881 | A1* | 12/2008 | Huang | A61B 3/024 382/131 |
| 2010/0111373 | A1* | 5/2010 | Chin | G06V 10/754 382/113 |
| 2011/0032533 | A1* | 2/2011 | Izatt | G06T 15/00 356/497 |
| 2012/0140174 | A1* | 6/2012 | Hee | A61B 3/102 351/246 |
| 2013/0128222 | A1* | 5/2013 | Huang | G06T 7/60 351/246 |
| 2014/0029820 | A1* | 1/2014 | Srivastava | A61B 3/102 382/131 |
| 2018/0014725 | A1* | 1/2018 | Bagherinia | G06T 7/215 |

OTHER PUBLICATIONS

Li, Yan, et al. "Corneal epithelial thickness mapping by Fourier-domain optical coherence tomography in normal and keratoconic eyes." Ophthalmology 119.12 (2012): 2425-2433.

Patrao, Lia Florim, et al. "Differentiation of mild keratoconus from corneal warpage according to topographic inferior steepening based on corneal tomography data." Arquivos brasileiros de oftalmologia 79.4 (2016): 264-267.

Tang, Maolong, et al. "Characteristics of keratoconus and pellucid marginal degeneration in mean curvature maps." American journal of ophthalmology 140.6 (2005): 993-1001.

* cited by examiner

Figure 5

DIAGNOSTIC CLASSIFICATION OF CORNEAL SHAPE ABNORMALITIES

CROSS REFERENCE TO RELATED APPLICATION

The present application is a U.S. Continuation Patent Application which claims priority to U.S. patent application Ser. No. 15/639,842 filed Jun. 30, 2017 and claims priority to U.S. Provisional Patent Application No. 62/357,198, titled "DIAGNOSTIC CLASSIFICATION OF CORNEAL SHAPE ABNORMALITIES," filed Jun. 30, 2016, the disclosure of which is hereby incorporated by reference in its entirety.

ACKNOWLEDGEMENT OF GOVERNMENT SUPPORT

This invention was made with the support of the United States government under the terms of grant number R01 EY018184 awarded by the National Institutes of Health. The United States government has certain rights to this invention.

FIELD

Generally, the disclosure is related to the field of ophthalmology. In particular, apparatuses, systems, and methods for the characterization and classification of corneal shape abnormalities are disclosed.

BACKGROUND

Conventional corneal topography is an important tool in the recognition of forme fruste (pre-clinical) keratoconus (FFK), an important risk factor for post-LASIK ectasia. However, the recognition of FFK on topographic displays such as axial power and tangential maps is a complex exercise because FFK can manifest as many possible patterns of distortion. Several tools have been developed to make the detection of FFK using corneal topographic data more reliable. The mean curvature (also referred to as mean power) map, for example, has been shown to better characterize keratoconus than the conventional axial and tangential power maps. This is because the mean curvature map contains information about both the radial and azimuthal curvature changes that occur in keratoconus, but is not confounded by regular astigmatism. In addition, more recent studies have shown that corneal pachymetry (i.e., corneal thickness) and epithelial thickness maps can be more sensitive than topography for keratoconus diagnosis.

None of these corneal maps on their own, however, can differentiate keratoconus from other corneal pathologies with similar topographic patterns, such as contact lens-related warpage, dry eye disease, and epithelial basement membrane dystrophy. Contact lens-related warpage of the cornea is of particular significance due to the prevalence of contact lens use in the population. Because many LASIK candidates are contact lens wearers, the distinction between contact lens-related warpage and FFK is a common diagnostic challenge faced by clinicians to ensure that post-LASIK ectasia outcomes are avoided. Therefore, there still exists a need for reliable methods to differentiate FFK from contact lens-related warpage.

BRIEF DESCRIPTION OF THE SEVERAL VIEWS OF THE DRAWINGS

FIG. 5 is a table that shows a comparison of group average data among normal, keratoconus, warpage, and forme fruste keratoconus subjects in a study conducted in accordance with Example 1 described herein.

FIG. 7A illustrates cross-sectional OCT (average of 5 repeated frames). FIG. 7B illustrates a MapWide scan pattern (diameter 9 mm, 12 radials, 1,536 axial scans each radial, repeated 5 times, acquisition time 1.3 second). FIG. 7C illustrates a magnified section of the OCT image. FIG. 7D illustrates a corneal axial scan.

DETAILED DESCRIPTION

Figure 1:
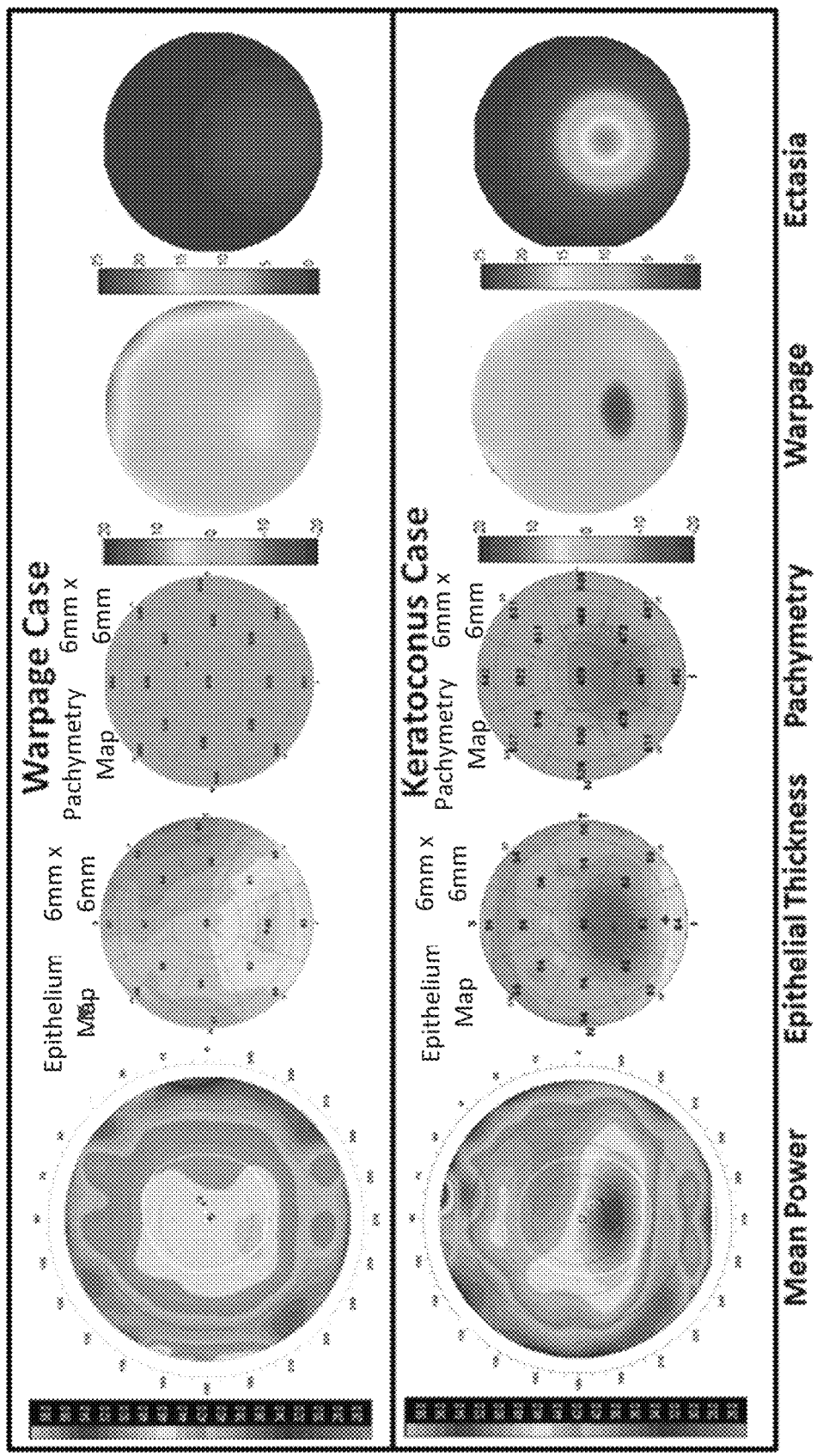
FIG. 1 is a set of example parameter maps for contact lens-related warpage (top) and keratoconus (bottom). Contact lens-related warpage and keratoconus conditions are not distinguishable by anterior topography (i.e., the mean power map) as both cases show inferior focal steepening. They can, however, be differentiated by the OCT epithelial map, which shows matching focal thickening in warpage and thinning in keratoconus. The pachymetry map shows focal thinning in keratoconus, but not in warpage. The warpage map is the product of the Pattern Deviation (PD) maps of anterior topography and epithelial thickness. The warpage map is predominantly positive for the warpage case (top) and predominantly negative for the keratoconus case (bottom). The ectasia map is the product of fitted Gaussian waveforms for the PD maps of anterior topography and pachymetry. It shows a clear cone-like pattern in keratoconus which is absent in warpage.

Disclosed are methods for characterizing corneal shape abnormalities. In some embodiments, the methods include combining the focal features represented in several types of corneal maps into indices which characterize different aspects of corneal shape or structure. The corneal maps may be generated from data derived from one or more imaging modalities, including optical coherence tomography (OCT), Scheimpflug corneal tomography, Placido topography, slit-scanning pachymetry, ultrasound imaging, or any other suitable means known in the art for measuring corneal properties. Specific corneal maps from which useful diagnostic indices may be derived using the disclosed methods include, but are not limited to, corneal topography maps, pachymetry maps, and epithelial thickness maps.

Disclosed herein are two novel diagnostic indices that combine features of shape abnormalities on different corneal maps: the Ectasia Index and the Warpage Index. The Ectasia Index combines focal corneal steepening/flattening on anterior/posterior topography with focal thinning/thickening on pachymetric maps by Gaussian fitting. In embodiments, the Ectasia Index can be used to identify keratoconic eyes. The Warpage Index combines focal corneal steepening/flattening on anterior/posterior topography with focal thinning/thickening on epithelial thickness maps by cross-correlation. The Warpage index can be used, for example, to identify eyes with contact lens-related warpage and other causes of corneal abnormalities, and to differentiate these conditions from pre-clinical keratoconus.

An aspect of the disclosed methods is that combining multiple cornea map features into indices makes automated classification of corneal conditions possible. In embodiments, the disclosed methods may provide an automated system for diagnosing ectatic conditions in the cornea and for differentiating pathologic and nonpathologic conditions. Further embodiments also include a computer-readable medium encoding the disclosed methods.

Also disclosed is a comprehensive classification system based on the above indices for differential diagnosis of corneal shape abnormalities that could be caused by keratoconus/ectasia, contact lens warpage, dry eye, and other conditions. Differential diagnosis of corneal shape abnormalities is of great practical significance in cornea, refractive surgery, and contact lens clinics, where the problem is not simply to distinguish keratoconus from normal. Rather, the greater challenge is the differential diagnosis of borderline corneal topographic distortion that could be caused by keratoconus/ectasia, contact lens, dry eye, and other conditions. In LASIK surgery in particular, it is important to identify patients having a predisposition to ectasia. In some embodiments of the methods described herein, LASIK surgery decision-making may be guided by utilizing a classification system to differentiate early stage or pre-clinical keratoconus conditions from non-pathological contact lens-related warpage, for example. The disclosed classification system can help clinicians take appropriate actions such as (1) no LASIK procedures for FFK patients, (2) contact lens abstention for patients with warpage, and (3) appropriate treatments for other causes of epithelial distortion such as dry eye or epithelium basement membrane dystrophy (EMBD).

In a particular embodiment of a classification system to differentiate keratoconus from warpage, pattern standard deviation (PSD) based on OCT epithelial thickness is used to detect corneal shape abnormalities and distinguish corneas with irregular shapes from corneas with normal shapes. For corneas classified as abnormal, the Warpage Index and Ectasia Index are calculated and utilized in a decision tree to further classify them as keratoconus without warpage, warpage without keratoconus, or keratoconus plus warpage.

An example method for classifying shape abnormalities of the cornea using the disclosed subject matter generally comprises: (a) generating cornea maps for a subject using anterior topography, epithelial thickness, and/or pachymetry; (b) calculating an epithelial PSD value, Warpage Index, and/or Anterior Ectasia Index; (c) comparing the epithelial PSD value, Warpage Index, and/or Anterior Ectasia Index to respective pre-determined threshold levels; and (d) classifying the subject's cornea condition based on the comparisons.

Additionally, a comprehensive system to differentiate between 3 causes of corneal shape irregularities: ectasia (e.g., keratoconus), epithelial deformations (e.g., contact lens warpage, epithelial dystrophy, dry eye), and non-ectatic stromal changes (e.g., scars, stromal dystrophy, LASIK) is provided. This system is based on OCT's unique ability to map epithelial thickness, pachymetry, and anterior/posterior topography. This system may be used in asymmetric keratoconus in which OCT may detect abnormalities in the better eye (FFK) that does not have clear abnormality on standard topography. Differentiation from other causes of corneal irregularities may also be provided. The comprehensive classification system may use the epithelial PSD, warpage index, anterior ectasia index, coincident-thinning (CT) index, and/or pachymetry-anterior topography (PAT) index to classify the cornea.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

Corneal topography is an essential part of LASIK preoperative workup to detect FFK and keratoconus, the most important risk factors of post-LASIK ectasia. However, topography is not sensitive to the very early stages of keratoconus when topographic steepening is masked by focal epithelial thinning. Furthermore, contact lens-related warpage can sometimes manifest as inferior steepening on topography with a pattern that is indistinguishable from keratoconus or FFK.

As an alternative to topography-based measures, diagnostic parameters based on optical coherence tomography (OCT) corneal pachymetry and epithelial thickness maps have been developed to help detect early keratoconus. These studies have shown that pattern standard deviation (PSD) based on OCT epithelial thickness—Epithelial PSD—is a particularly effective parameter for differentiating keratoconus from normal eyes, including manifestations of subclinical keratoconus. For example, in a group of 50 subclinical keratoconus (CDVA 20/20 or better) and 150 normal control eyes, Epithelial PSD was able to detect early keratoconus with sensitivity of 96% at 100% specificity (Li Y, Chamberlain W, Tan O, et al. Subclinical keratoconus detection by pattern analysis of corneal and epithelial thickness maps with optical coherence tomography. J Cataract Refract Surg 2016; 42(2):284-95, incorporated by reference herein). Furthermore, Epithelial PSD has been shown to be effective in detecting abnormality in keratometry, I-S (inferior-superior dioptric asymmetry), skew percentage, astigmatism (KISA)-normal FFK eyes.

While Epithelial PSD is very sensitive at detecting the focal epithelial thinning that masks early ectasia on anterior topography, it is also very sensitive at detecting the uneven epithelium variation that characterizes contact lens-related warpage and other corneal surface distortions. Thus, Epithelial PSD alone is unable to effectively differentiate FFK from contact lens-related warpage or other corneal abnormalities. Consequently, alternate approaches are needed for effective diagnosis. One approach is to combine information from multiple different corneal maps to characterize corneal shape abnormalities.

Disclosed herein are two novel indices, the Anterior Ectasia Index and the Warpage Index, that have utility in differentiating keratoconus from corneal warpage. These indices are calculated by combining the focal changes captured in anterior corneal topography maps with corneal pachymetry maps and epithelial thickness maps, respectively. In the current state of the art, keratoconus diagnostic algorithms only attempt to distinguish keratoconus from normal eyes. The approach described herein provides a means to differentiate keratoconus eyes from both normal and pathological eyes, including eyes having contact lens-related warpage. As such, it is more closely tailored to the real-world application where a surgeon must distinguish between several different conditions that require different treatment decisions.

The methodology described herein relies on the mapping of corneal parameters from different data acquisition modalities such that they reflect the deviation from an anatomically normal cornea. These maps are referred to as pattern deviation (PD) maps. The PD map can be defined as the percent deviation from the normal reference map (e.g., the average map of a healthy control group). In the present disclosed embodiment, PD can be calculated based on topography, pachymetry, or epithelial thickness data, but other measurable corneal properties may also be represented in the form of PD maps. Detailed methods for calculating the PD map have been described in a previous study (see Li Y, Tan O, Brass R, et al. Corneal epithelial thickness mapping by Fourier-domain optical coherence tomography in normal and keratoconic eyes. Ophthalmology 2012; 119(12):2425-33, the content of which is incorporated by reference herein in its entirety). The normal reference maps were also established in that study. The Epithelial pattern standard deviation (PSD) parameter is calculated as the root-mean-square value of the epithelial thickness PD map described previously.

The Warpage Index disclosed herein was designed based on the insight that anterior focal steepening is accompanied by focal epithelial thickening in contact lens-related warpage, but associated with epithelial thinning in keratoconus (see Table 1).

TABLE 1

Focal Changes that Differentiate Keratoconus from Warpage on Corneal Maps

| | Pachymetry | Anterior Topography | Epithelial Thickness |
|---|---|---|---|
| Keratoconus | Thinning | Steepening | Thinning |
| Warpage | No change | Steepening Flattening | Thickening Thinning |

The Warpage Index is calculated by the cross-correlation of the PD maps of anterior topography and epithelial thickness as shown in Equation 1 below:

$$\text{Warpage Index} = 100 * \text{sign}(PD_{Ant} \cdot PD_{Epi}) * \sqrt{|PD_{Ant} \cdot PD_{Epi}|} \quad \text{(Equation 1)}$$

where $PD_{Ant}$ is the PD map of anterior mean curvature, and $PD_{Epi}$ is the PD map of epithelial thickness. A positive value of the Warpage Index indicates warpage, while a negative value indicates keratoconus, as shown in FIG. 1.

Although a negative Warpage Index is consistent with keratoconus, pachymetry map information may also incorporated into another parameter, the Anterior Ectasia Index, to further confirm the classification. A Gaussian waveform, which is cone shaped, may be used to fit the focal ectasia on the anterior surface of the cornea (e.g., as described in Tang M, Shekhar R, Miranda D, Huang D. Characteristics of keratoconus and pellucid marginal degeneration in mean curvature maps. Am J Ophthalmol 2005; 140(6):993-1001, which is incorporated by reference herein). The fitted Gaussian waveform may be combined with corneal pachymetry data using the multiplicative formula shown in Equation 2 below to capture coincident focal topographic steepening and pachymetric thinning (e.g., as shown in Table 1).

$$\text{Anterior Ectasia Index} = 100 * \sqrt{\text{Max}(G_{Ant} * G_{Pachy})} \quad \text{(Equation 2)}$$

where $G_{Ant}$ and $G_{Pachy}$ are the best-fit Gaussian waveforms for the PD maps of anterior mean curvature and corneal pachymetry. The value of the Anterior Ectasia Index is the magnitude of the combined Gaussian waveforms and indicates percentage deviation from the normal reference. In alternate embodiments, another mathematical function may be used for the fitting of the corneal data, including Zernike polynomials, an Alpha function, a Rayleigh function, or a Cauchy function.

An abnormally high Anterior Ectasia Index is the result of the coincident focal topographic steepening and pachymetric thinning, which is typical in keratoconus and other ectasias (e.g., pellucid marginal degeneration and post-LASIK ectasia) but not in warpage (see Table 1). An abnormal (i.e, positive) Warpage Index reflects focal topographic steepening and flattening due to focal epithelial thickening and thinning. Most normal eyes have a small positive Warpage Index, suggesting that there is some degree of naturally-occurring warpage in normal eyes. This natural warpage may be caused by upper lid pressure molding the epithelial thickness, causing the characteristic normal pattern of slightly thinner superior epithelium and slightly flatter superior topography. Contact lens wear, however, causes an uneven pressure distribution on the epithelium and produces more variable warpage patterns across the cornea. Thus, the Warpage Index parameter is well-suited to distinguish contact lens-associated warpage from naturally occurring warpage. In some embodiments, the warpage threshold used to classify the cornea as warpage (e.g., contact lens-associated warpage) may be zero (e.g., a positive Warpage Index may be classified as warpage, while a negative Warpage Index may be classified as no warpage). In other embodiments, the warpage threshold may have a positive value (e.g., to distinguish between naturally-occurring warpage and contact lens-associated warpage).

Using either the Anterior Ectasia Index or the Warpage Index alone is insufficient to distinguish between keratoconus and warpage. Although the Anterior Ectasia Index can effectively separate the keratoconus and normal groups, it cannot differentiate between the warpage and normal groups. Similarly, although Warpage index is positive in all warpage eyes and negative in most keratoconus eyes, it cannot discriminate cases where keratoconus and warpage co-exist. Thus, a tripartite classification between normal, warpage, and ectasia conditions requires the use of both the Anterior Ectasia Index and the Warpage Index together with the Epithelial PSD.

Figure 4:
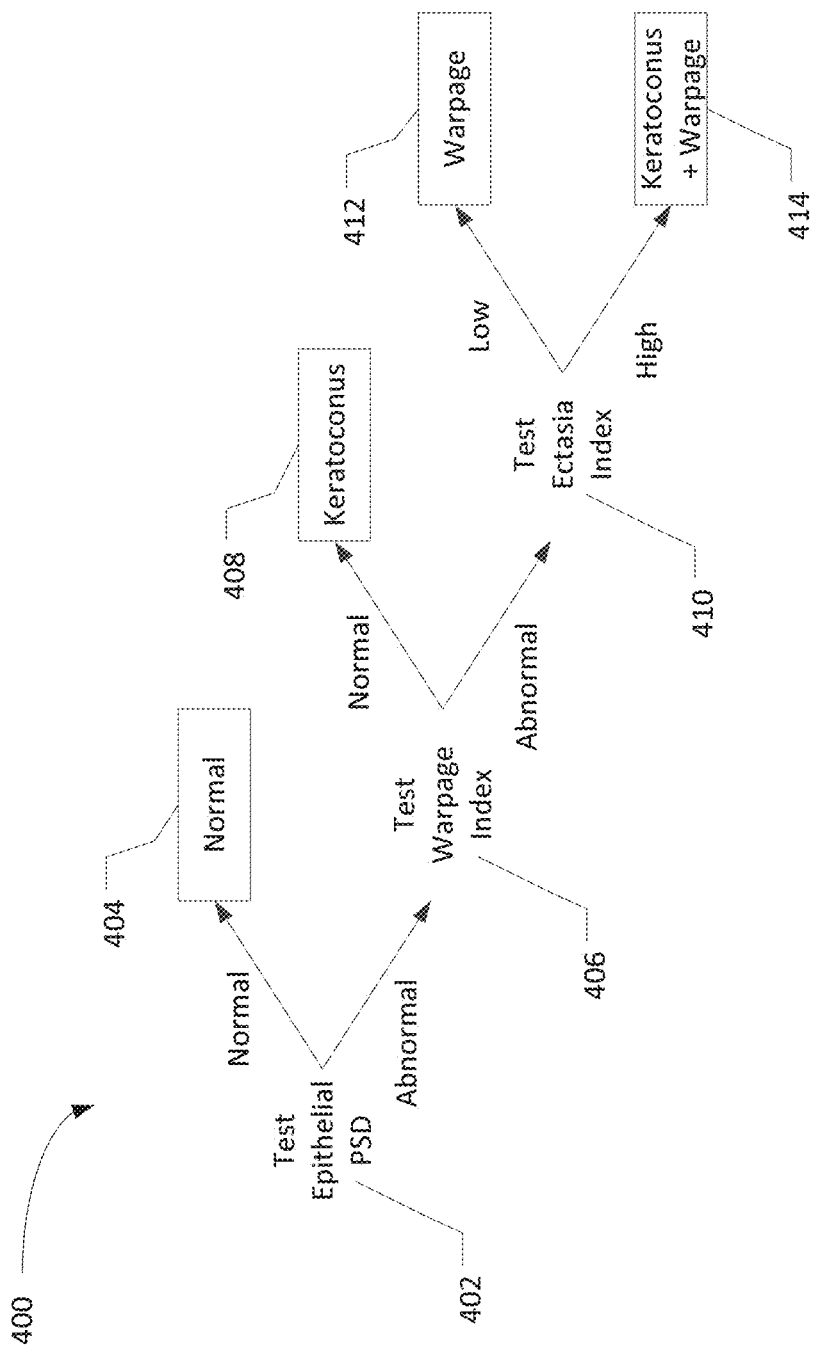
FIG. 4 is example decision tree for an irregular cornea classification process (e.g., for keratoconus and warpage diagnosis) in a clinical setting, in accordance with various embodiments.

Various embodiments of a tripartite classification scheme may use a decision tree. FIG. 4 shows an example decision tree 400 that may be followed as part of a classification process for a subject's eye as described herein. At 402, the process may include determining whether the Epithelial PSD of the eye is normal (e.g., below a threshold) or abnormal (e.g., above the threshold). The Epithelial PSD may have the highest accuracy for separating normal from abnormal corneas. If the Epithelial PSD is determined to be normal, then the subject's eye is determined to be normal at 404. However, if the Epithelial PSD is determined to be abnormal (e.g., abnormally high), then the process proceeds to look at (e.g., test) the Warpage Index at 406.

If, at 406, the Warpage Index is determined to be normal (e.g., negative), then the subject's eye is determined to have keratoconus at 408 (e.g., keratoconus without warpage). However, if, at 406, the Warpage Index is determined to be abnormal (e.g., positive), the subject's eye is determined to have warpage. At 410, the subject's eye with warpage is tested with the Anterior Ectasia Index. If, at 410, the Anterior Ectasia Index is determined to be low (e.g., below a threshold), then the subject's eye is determined to have warpage without keratoconus (e.g., pure warpage) at 412. If, at 410, the Anterior Ectasia Index is determined to be high (e.g., above the threshold), then the subject's eye is determined to have both keratoconus and warpage at 414.

In various embodiments, a variation of the classification process described above with reference to FIG. 4 may be used to additionally or alternatively identify stromal changes in the eye. Standard topography cannot distinguish ectasia from other causes of focal anterior steepening. The conditions that sometimes mimic ectasia include epithelial changes (e.g., contact lens-related warpage, epithelial basement membrane dystrophy) and stromal changes (e.g., decentered hyperopic LASIK).

Accordingly, an OCT-based classification system to differentiate between the causes of corneal shape irregularities: ectasia, epithelial deformations, and non-ectatic stromal changes, is provided. The classification system is based on the unique ability of OCT to provide high-resolution maps of both anterior and posterior topographies, as well as maps of epithelial thickness and pachymetry. Composite indices based on the 4 types of OCT maps may correctly classify FFK (not wearing contact lenses) and contact lens-related warpage with 100% accuracy. This further supports the teachings described above that parameters combining different types of OCT maps can be effective in the classification of corneal irregularities. Such a classification system could not be developed using standard technologies such as Placido-disc topography and Scheimpflug tomography, neither of which could map epithelial thickness. The OCT-based classification system described herein will improve the sensitivity of detecting FFK as well distinguishing it from other types of common corneal conditions—a significant advance over current automated keratoconus diagnostic algorithms, which only distinguish between keratoconus and normal eyes.

As discussed above, OCT may be used for the mapping of corneal thickness (pachymetry) and epithelial thickness, and these maps may be used for keratoconus diagnosis. For example, the Epithelial PSD may be used to diagnose keratoconus, which is 100% accurate for keratoconus diagnosis, and also nearly perfect for subclinical keratoconus diagnosis. Furthermore, Epithelial PSD can detect abnormality in the better eye of "asymmetric" keratoconus that was missed by corneal topography. However, the Epithelial PSD cannot differentiate between keratoconus and other corneal conditions. Accordingly, a multi-map analysis may be used to differentiate the causes of corneal irregularities.

Figure 6:
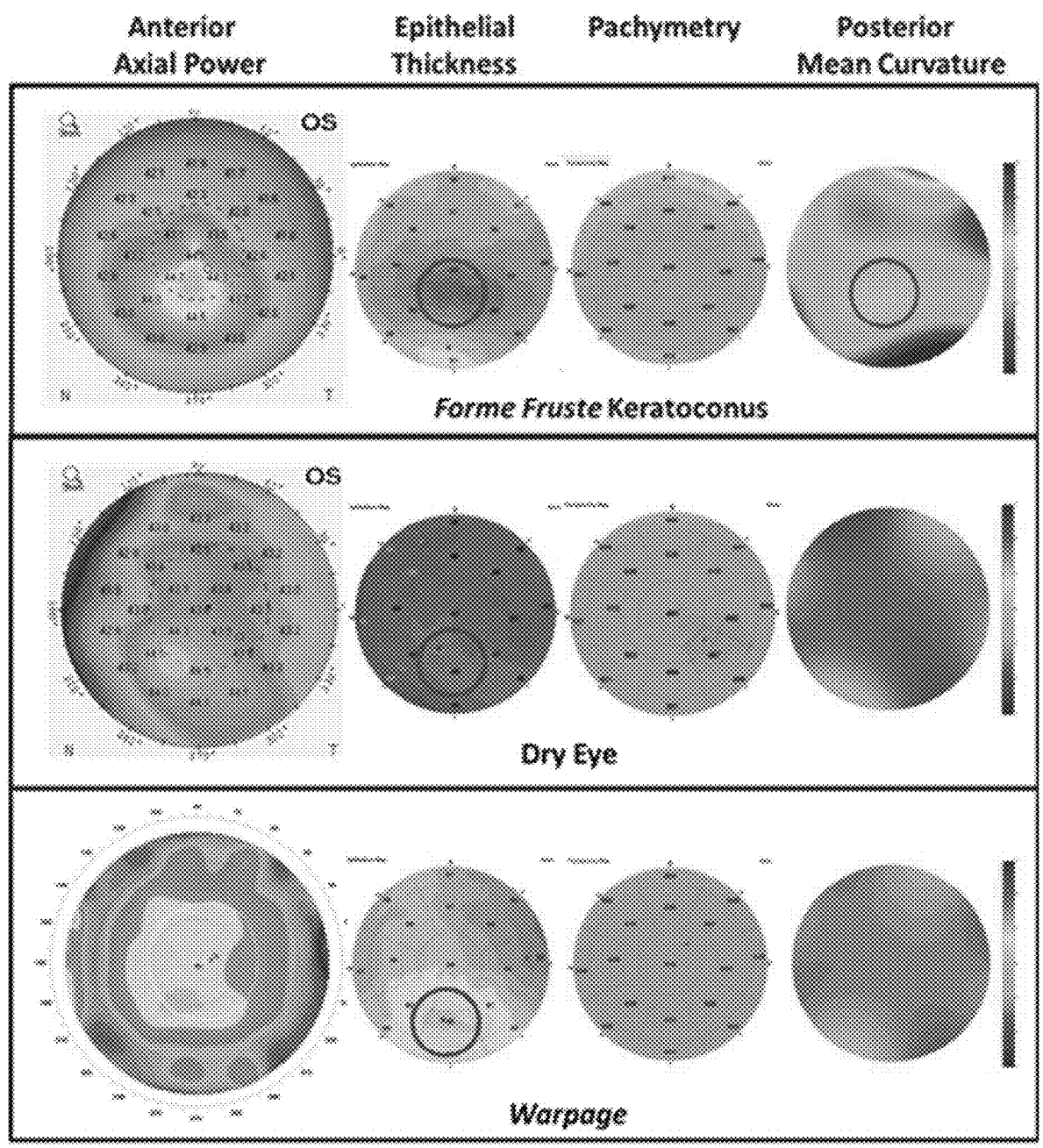
FIG. 6 illustrates maps of anterior axial power, epithelial thickness, pachymetry, and posterior mean curvature for respective corneas having FFK, dry eye, or warpage, in accordance with various embodiments. FFK is often diagnosed by inferior focal steepening on anterior axial topography. However, as shown, dry eye and contact lens related warpage can show a similar pattern. These conditions can be distinguished by OCT, which shows coincident focal epithelial thinning (circle on epithelial thickness map in FFK case) only in FFK, in contrast to inferior focal epithelial thickening (denoted by circles in epithelial thickness maps) in the dry eye and warpage cases. A coincident focal pachymetric thinning and posterior steepening (denoted by circle in posterior mean curvature map) are also only found in FFK.

As shown in FIG. 6, even early FFK may be recognized by coincident focal anterior/posterior steepening and epithelial/pachymetric thinning. In contrast, dry eye and contact lens-related warpage have focal epithelial thickening with anterior steepening. FFK is often diagnosed by inferior focal steepening on anterior axial topography. However, dry eye and contact lens related warpage can show a similar pattern. These conditions may be distinguished by OCT, which shows coincident focal epithelial thinning (denoted by circle on epithelial thickness map for FFK case) only in FFK, in contrast to inferior focal epithelial thickening (denoted by circles) in the dry eye and warpage cases. A coincident focal pachymetric thinning and posterior steepening (denoted by circle in posterior mean curvature map) are also found in FFK.

The classification system described herein further extends the OCT classification system to other types of conditions. To date, all keratoconus diagnostic algorithms only attempt to distinguish keratoconus from normal eyes. In contrast, the classification system described herein is better tailored to the real-world application where the surgeon faces multiple choices of differential diagnoses and treatments, rather than a simplified binary clinical study.

Figure 9:
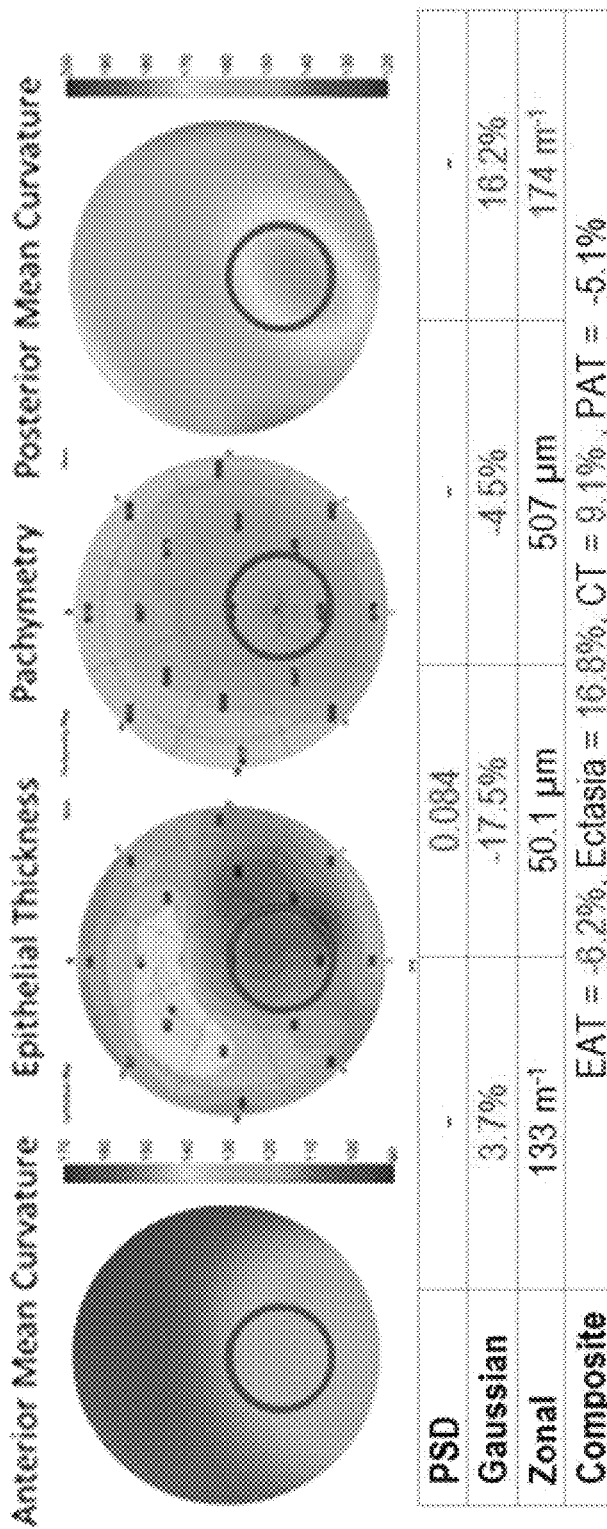
FIG. 9 illustrates maps of anterior mean curvature, epithelial thickness, pachymetry, and posterior mean curvature, and OCT parameters of a hard contact lens wearing FFK left eye. These parameters may be used as input to a Random Forests classifier for detection and classification of corneal shape irregularities. Note coincident shape abnormalities in the ectasia zone (marked by circle) on each map centered on the location of minimum Gaussian filtered pachymetry. The Gaussian parameters were all abnormal, demonstrating detection of ectasia—note posterior steepening is 4 times anterior, and focal epithelial thinning is 4 times the pachymetric thinning on a percent basis. There was inferior epithelial thinning due to FFK and temporal thinning due to contact lens. The zonal average posterior mean curvature was abnormally high indicating focal steepening. Of the 3 abnormal composite indices (EAT, ectasia, and CT), EAT was negative indicating compensatory epithelial modulation, while Ectasia and CT indices were high confirming classification as ectasia. Other OCT parameters that may serve as inputs include vertical location of thinnest pachymetry/epithelium or maximum mean curvature, asymmetry measures (inferior-superior, inferotemporal-superonasal), and/or thinning measures (minimum, minimum-median). PSD refers to pattern standard deviation, and zonal refers to the average value within the ectasia zone. The examples in FIG. 9 used 6-mm maps from Avanti OCT. Other embodiments may use different size maps, such as 9 or 10-mm maps (see Table 2).

Additionally, OCT metrics for detecting progression of keratoconus may be provided. Epithelial thickness and posterior mean curvature are more sensitive to keratoconus than conventional anterior topography and pachymetry (see FIG. 9, discussed further below). Zonal average and Gaussian fitting in the ectasia zone may enhance (e.g., maximize) sensitivity to focal ectasia while improving reproducibility by analyzing a broad area.

Figure 8:
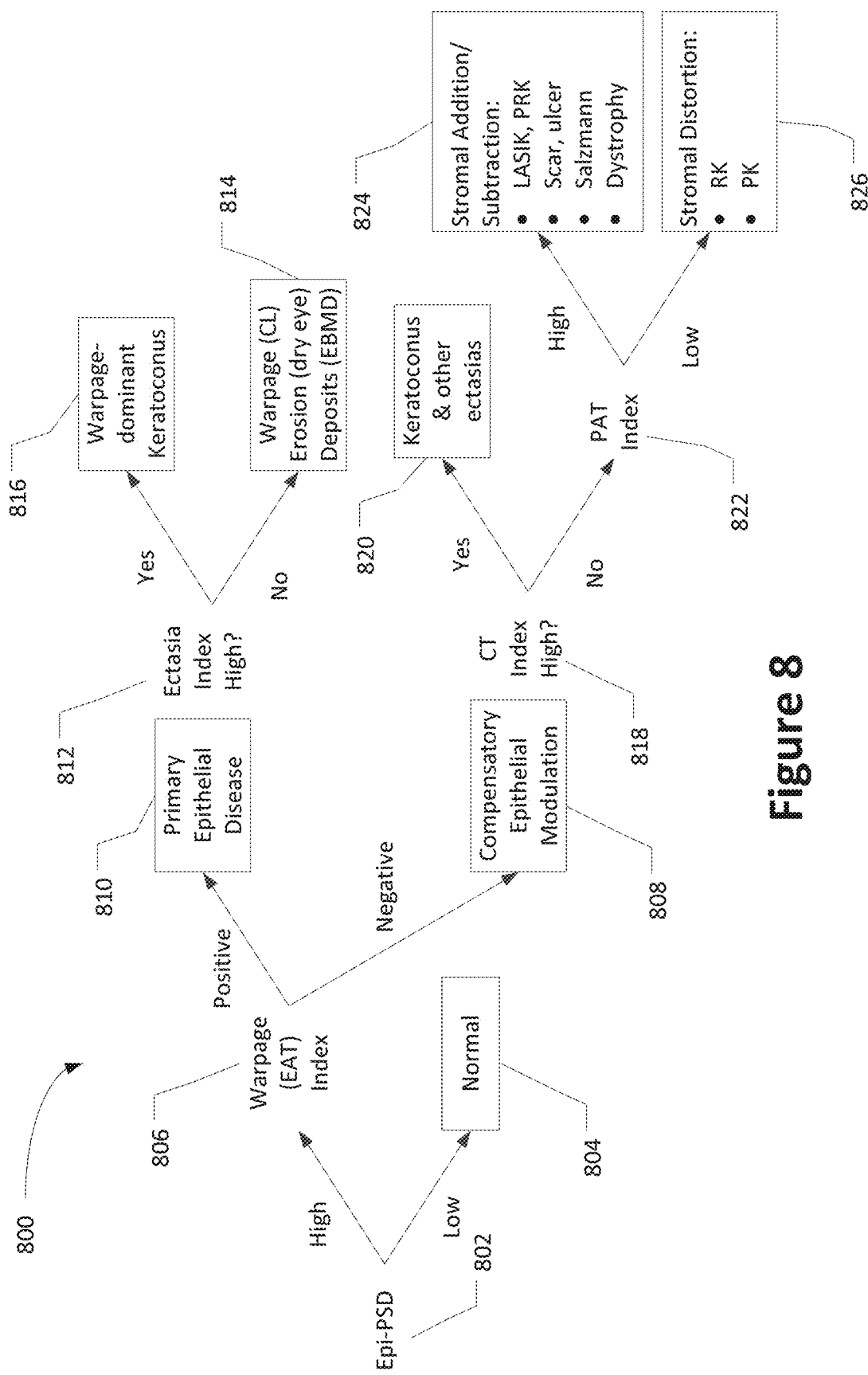
FIG. 8 is another example decision tree for a comprehensive cornea classification process, in accordance with various embodiments.

FIG. 8 illustrates a decision tree for a comprehensive classification process 800 to classify a subject's eye (e.g., the cornea of the eye) in accordance with various embodiments. The comprehensive classification process 800 may distinguish between various types of corneal shape irregularities including ectasia, epithelial deformations, and non-ectatic stromal changes.

At 802, the process 800 may include determining whether the Epithelial PSD of the eye is normal (e.g., below a Epithelial PSD threshold) or abnormal (e.g., above the Epithelial PSD threshold). As discussed, the Epithelial PSD may have the highest accuracy for separating normal from abnormal corneas. If the Epithelial PSD is determined to be normal, then the subject's eye is determined to be normal at 804. However, if the Epithelial PSD is determined to be abnormal (e.g., abnormally high), then the process proceeds to look at (e.g., test) the Warpage Index (also referred to as the Epithelium Anterior Topography (EAT) Index) at 806.

If, at 806, the Warpage Index is determined to be below a warpage threshold (e.g., negative), then the subject's eye is determined to have compensatory epithelial modulation at 808. However, if, at 806, the Warpage Index is determined to be above the warpage threshold (e.g., positive), the subject's eye is determined to have primary epithelial disease (e.g., warpage) at 810. If the subject's eye is determined to have primary epithelial disease, then, at 812, the subject's eye is tested with the Anterior Ectasia Index. If, at 812, the Anterior Ectasia Index is determined to be low (e.g., below a threshold), then the subject's eye is determined to have warpage without keratoconus (e.g., pure warpage), erosion (dry eye), and/or deposits (EBMD) at 814. If, at 812, the Anterior Ectasia Index is determined to be high (e.g., above the threshold), then the subject's eye is determined to have both keratoconus and warpage at 816 (e.g., warpage-dominant keratoconus).

Returning to block 808, if the subject's eye is determined to have compensatory epithelial modulation at 808, then the Coincident-Thinning (CT) Index of the eye may be tested at 818. If the CT Index is greater than a CT threshold, then the eye may be determined to have keratoconus and other ectasias at 820. If the CT Index is less than the CT threshold, then Pachymetry-Anterior Topography (PAT) Index may be tested at 822. If the PAT Index is higher than a PAT threshold, then the eye may be determined to have stromal addition or subtraction (e.g., LASIK, photorefractive keratectomy (PRK), scar, ulcer, Salzmann's nodular degeneration (Salzmann), and/or dystrophy) at 824. If the PAT Index is lower than the PAT threshold, then the eye is determined to have stromal distortion (e.g., radial keratotomy (RK), penetrating keratoplasty (PK)) at 826.

The comprehensive classification process 800 will be discussed further below with reference to Example 2, including additional information on the parameters to be tested and the associated conditions.

EXAMPLES

The following examples are illustrative of the disclosed methods. In light of this disclosure, those skilled in the art will recognize that variations of these examples and other examples of the disclosed method would be possible without undue experimentation.

Example 1

Purpose: To differentiate between keratoconus and contact lens-related corneal warpage by combining focal change patterns in anterior corneal topography, pachymetry, and epithelial thickness maps.

Methods: Pachymetry and epithelial thickness maps of normal, keratoconus, and warpage, and forme fruste keratoconus (FFK) eyes were obtained from a Fourier-domain OCT. Epithelial pattern standard deviation (PSD) was calculated and combined with two novel indices, the Warpage Index and the Anterior Ectasia Index, to differentiate between normal, keratoconus and warpage eyes. The values of the three parameters were compared between groups.

Subjects: A prospective observational study was approved by the institutional review board of the Casey Eye Institute, Portland, Oreg., USA. The work was compliant with the Health Insurance Portability and Accountability Act of 1996 and adhered to the tenets of the Declaration of Helsinki. Normal subjects enrolled in this study were LASIK candidates who had no ocular diseases and had not been wearing contact lenses for at least 2 weeks prior to the exams. Keratoconus subjects included in this study were diagnosed clinically with the following inclusion criteria: topography characteristic of keratoconus (e.g., as described in Binder P S, Lindstrom R L, Stulting R D, et al. Keratoconus and corneal ectasia after LASIK. Journal of cataract and refractive surgery 2005; 31(11):2035-8, incorporated by reference herein) (for example, skewed asymmetric bow-tie, inferior steep spot, or claw patterns), KISA % index (e.g., as described in Rabinowitz Y S, Rasheed K. KISA % index: a quantitative videokeratography algorithm embodying minimal topographic criteria for diagnosing keratoconus. J Cataract Refract Surg 1999; 25(10):1327-35) greater than 100, and best spectacle-corrected visual acuity (BSCVA) 20/25 or worse. Eyes with late keratoconic changes such as corneal scars or hydrops were excluded as they did not pose any diagnostic challenge. Keratoconus participants were subdivided into those who used rigid gas-permeable (RGP) contact lenses and those who did not. There were no keratoconus participants who used soft contact lens. Contact lens warpage was defined as contact lens wearers having a topographic abnormality. The topographic abnormality included inferior-superior asymmetry greater than 1.4 D or 5-mm zone irregularity index>1.5 D on a slit-scanning topographer (Orbscan II, Bausch & Lomb, Rochester, N.Y., USA). The FFK cases in the study were the better (i.e., less symptomatic) eyes of asymmetric keratoconus subjects. These eyes were all KISA normal (KISA %<60) with the contralateral eyes having keratoconus as per the prior diagnostic criteria.

Topography and OCT: Anterior corneal topography was obtained and exported from the Orbscan II device (Bausch & Lomb, Bridgewater, N.J.). This system projects 40 optical slits, 20 from the right and 20 from the left, onto the cornea at a 45-degree angle. The resulting slit images are captured by a digital video camera and used to reconstruct the topography of corneal surface. The topography maps were repositioned to be centered on the pupil center. The KISA % index was calculated based on the Placido-based axial power maps from the Orbscan II. A Fourier-domain OCT system (RTVue, Optovue, Fremont, Calif., USA) was used to acquire corneal pachymetry and epithelial thickness maps. The system works at an 830 nm wavelength and has a scanning speed of 26,000 axial scans per second. The depth resolution of RTVue is 5 µm (full-width-half-maximum) in tissue. The OCT scan pattern for mapping the cornea was "Pachymetry+CPwr" which consisted of 8 evenly-spaced radial scans 6 mm in length. The pachymetry and epithelial thickness maps were also centered on the pupil center.

Image Processing and Statistical Analysis: Image processing was performed using MATLAB version 5.3 (Mathworks, Natick, Mass.). Statistical analysis was performed using Excel (Microsoft Corp, Redmond, Wash.) and SPSS 20 (IBM, Armonk, N.Y.). A generalized estimation equation model (e.g., as described in Liang K Y, Zeger S L. Longitudinal data analysis using generalized linear models. Biometrika 1986; 73(1):13-22, incorporated by reference herein) was used to account for the correlation between the eyes of the same subject. Kruskal-Wallis nonparametric tests were used to compare different groups.

Figure 5:
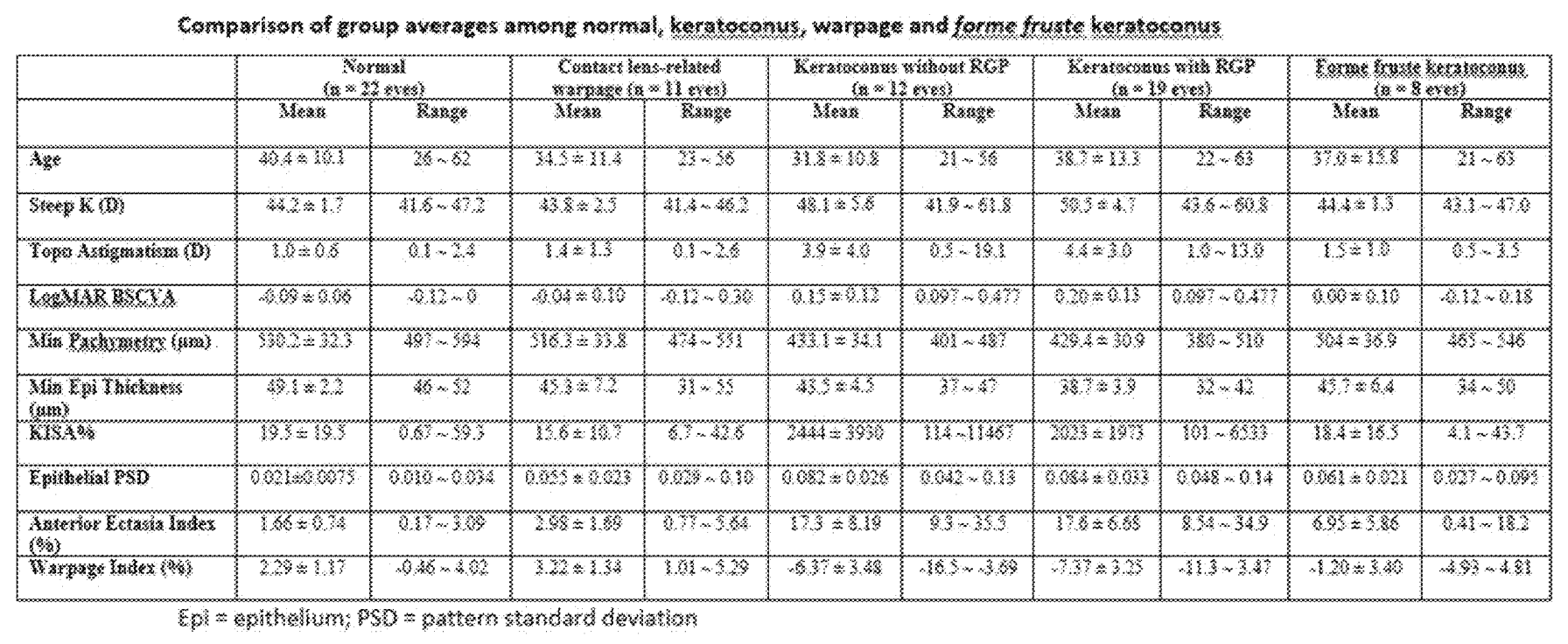

Results: The study included 31 keratoconic eyes (19 of which had recent RGP contact lens wear) of 20 subjects, 22 normal eyes of 11 subjects, 11 eyes (6 eyes wearing RGP contact lenses, 5 eyes wearing soft toric contact lenses) of 8 subjects with contact lens-related corneal warpage and 8 FFK eyes (4 of which had recent RGP contact lens wear) of 8 subjects. FIG. 5 shows a comparison of group averages, among normal, keratoconus, warpage, and forme fruste keratoconus subjects. There was no difference in age between groups. The keratoconus group had significantly higher steep K, topographic astigmatism, KISA %, and lower minimum pachymetry than those in normal, warpage and FFK groups. The minimum epithelial thickness in the keratoconus group was significantly lower than that in the normal group but was not different from that in the warpage or the FFK group.

The Epithelial PSD was normal (0.021±0.0075; mean±standard deviation) for all normal eyes (100% specificity) based on a previously published diagnostic threshold of 0.041, which was 2.33 standard deviation above the mean (99 percentile of normal distribution) of 150 eyes in a normal reference group (e.g., as described in Li Y, Chamberlain W, Tan O, et al. Subclinical keratoconus detection by pattern analysis of corneal and epithelial thickness maps with optical coherence tomography. J Cataract Refract Surg 2016; 42(2):284-95, incorporated by reference herein). The Epithelial PSD was abnormally high for all (100% sensitivity) keratoconic (0.083±0.034), 9 out of 11 (81.8% sensitivity) warpage eyes (0.055±0.023), and 7 out of 8 (87.5% sensitivity) FFK eyes (0.061±0.021). The Epithelial PSD values for the keratoconus group, warpage group and FFK group were all significantly (p<0.001) higher than normal (see Table in FIG. 5). There was no difference in mean Epithelial PSD values between eyes with RGP contact lens-induced warpage and eyes with soft toric contact lens-induced warpage.

The Anterior Ectasia Index was correlated with KISA % (Pearson's r=0.60) in the keratoconus group but not in the normal (r=0.14), warpage (r=0.16), or the FFK group (r=0.076) The Anterior Ectasia Index for the normal group (1.66±0.74) was significantly lower than that for the keratoconus group (17.5±7.17, p<0.001), the warpage group (2.98±1.69, p=0.0063) and the FFK group (6.95±5.86, p<0.001). Using Anterior Ectasia Index of 6.92, 2.33 standard deviation above the mean (99 percentile of normal distribution) of the warpage group as the cutoff, there was 100% sensitivity and specificity in detecting keratoconus. Four of the FFK eyes had abnormally high Anterior Ectasia Index (see FIG. 2).

Figure 2:
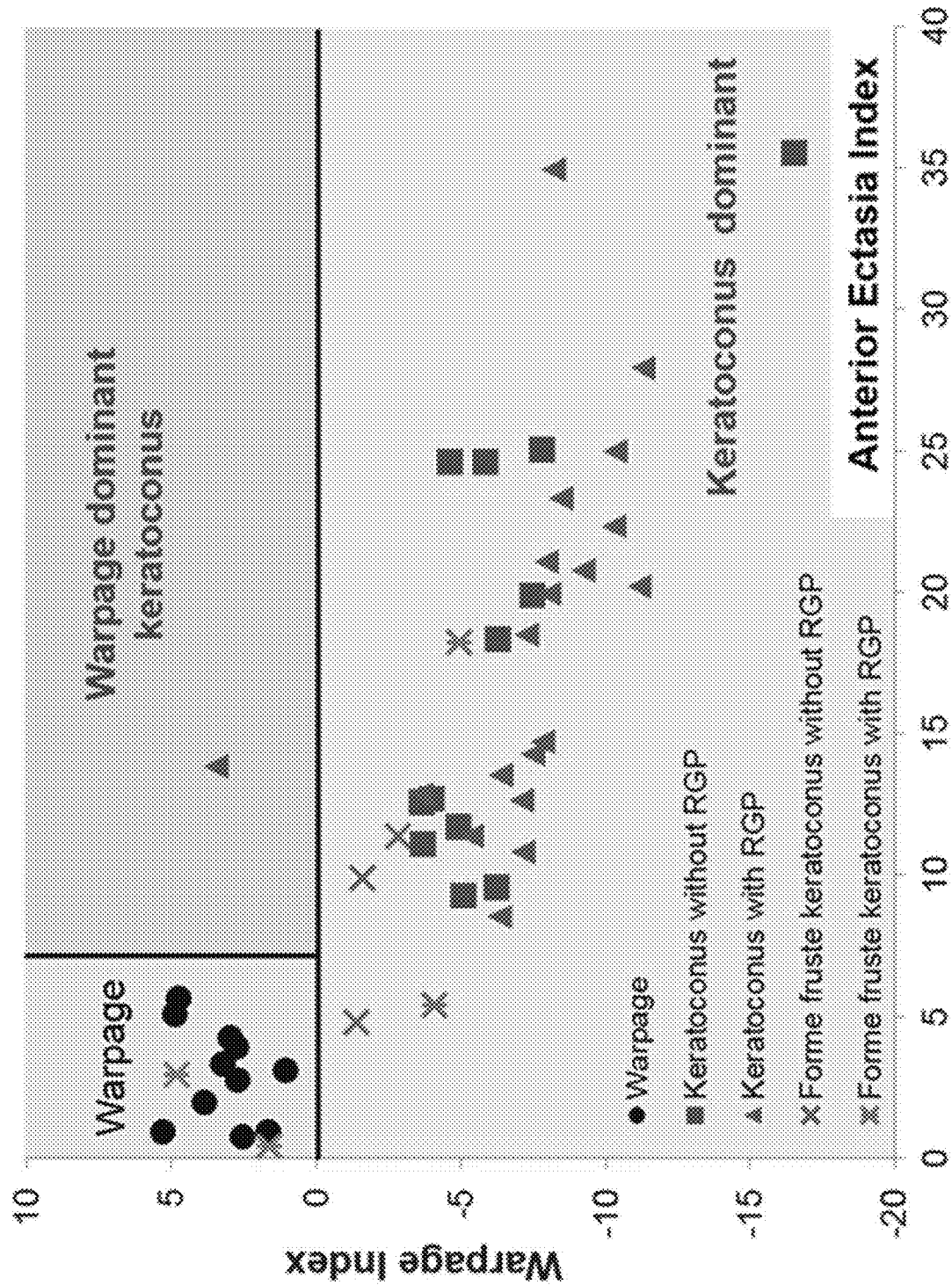
FIG. 2 is a plot of Warpage Index versus Anterior Ectasia Index. The Anterior Ectasia Index and Warpage Index can be used to differentiate warpage from keratoconus for eyes with abnormal Epithelial pattern standard deviation (PSD) values. The pink area denotes keratoconus, while the blue area denotes warpage. The purple area indicates both conditions coexist. RGP refers to a rigid gas-permeable contact lens.
Figure 3:
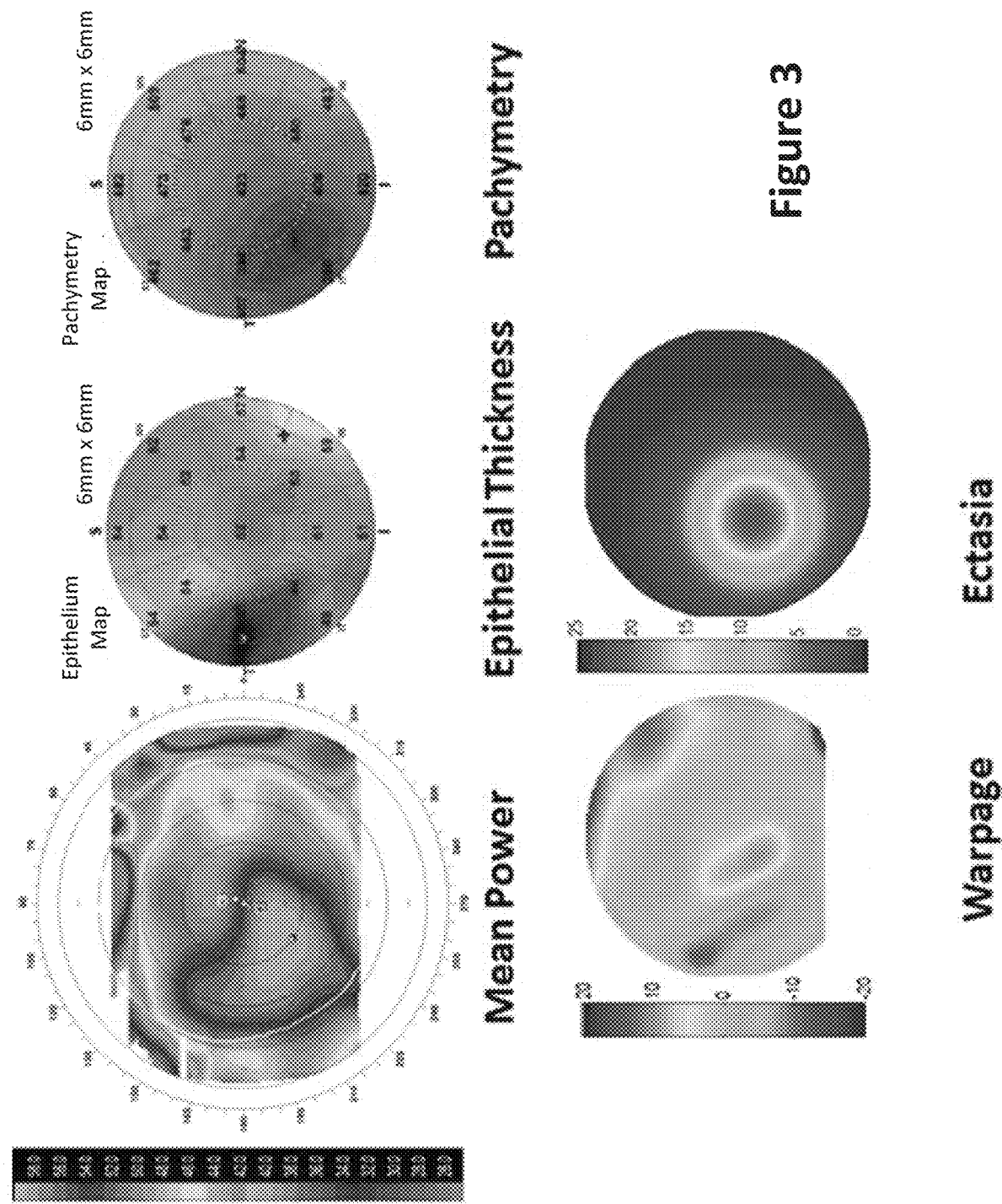
FIG. 3 is a set of parameter maps for an example keratoconus case which also shows signs of contact-lens related warpage.

The Warpage Index was positive in all warpage eyes (3.22±1.34) and all (2.29±1.17) except one normal eye. The Warpage Index was negative for all (−6.98±3.32) except one keratoconus eyes (FIG. 2). The one keratoconus eye with positive Warpage Index was a RGP wearer as shown in FIG. 3. The keratoconus with RGP group tended to have a slightly more negative Warpage Index (−7.37±3.25) than that in keratoconus without RGP group (−6.37±3.48) but the difference was not statistically significant (p=0.78). Among the 7 FFK eyes with abnormal Epithelial PSD, five had negative Warpage Index values. The other 2 had positive Warpage Index and were both RGP contact lens wearers (FIG. 2).

Contact Lenses: All warpage cases in the study presented herein (see Examples section below) were induced by RGP or soft toric contact lenses rather than regular soft spherical lenses, suggesting that RGP and soft toric contact lenses had more effect in changing the corneal epithelium. Although the study presented herein did not include subjects with dry eye or epithelial basement membrane dystrophy, these conditions should also produce uneven epithelium and increase both the Epithelial PSD and Warpage Index.

In most keratoconic eyes wearing RGP contact lenses, there was an abnormally high Anterior Ectasia Index and a negative Warpage Index. This is contrary to the positive Warpage Index seen in non-keratoconic contact lens warpage. Furthermore, the keratoconus/RGP eyes tend to have more negative Warpage Index values than keratoconic eyes without contact lenses (FIG. 2). This may be because epithelium at the cone peak comes into contact with the RGP contact lenses, resulting in epithelial thinning at a location of topography steepening—the opposite of the typical warpage pattern where epithelial thinning is associated with focal topographic flattening. In the one keratoconus/RGP case where the Warpage Index was positive (FIG. 3), the cone apex was off-center inferotemporally, and the RGP-related warpage caused focal epithelium thickening that shifted the location of topographic steepening superonasally toward the central cornea. Overall, in RGP-wearing keratoconus eyes, there is a paradoxical negative shift of the Warpage Index due cone-apex RGP touch, except in the unusual case where the RGP-corneal contact is not at the cone apex.

Classification Results: Classification of eye conditions was performed using the decision tree described previously (e.g., the decision process shown in FIG. 4). Using this scheme, all of the normal (100% specificity) and keratoconic eyes (100% sensitivity) were correctly classified. Nine of the contact lens-related warpage cases were correctly classified (81.8% sensitivity), while 2 were misclassified as normal. One of the 19 RGP-corrected keratoconus eyes had mixed keratoconus plus warpage pattern, while in 18 of them the keratoconus pattern predominated. Five out of 8 FFK eyes (62.5% sensitivity) were correctly classified. The 3 misclassified FFK eyes included one having normal Epithelial PSD (misclassified as normal) and 2 wearing RGP contact lenses (misclassified as warpage).

Conclusions: The Epithelial PSD can distinguish normal from keratoconus or warpage with high sensitivity and specificity, but does not distinguish between these two conditions. The Anterior Ectasia Index is abnormal (i.e., high) in keratoconus but not warpage. The Warpage Index is positive for warpage and negative for keratoconus, except in cases where keratoconus and warpage co-exist. Together, the 3 parameters are strong tripartite discriminators of normal, keratoconus, and warpage conditions.

Example 2

Approach—OCT Technology

Figure 7:
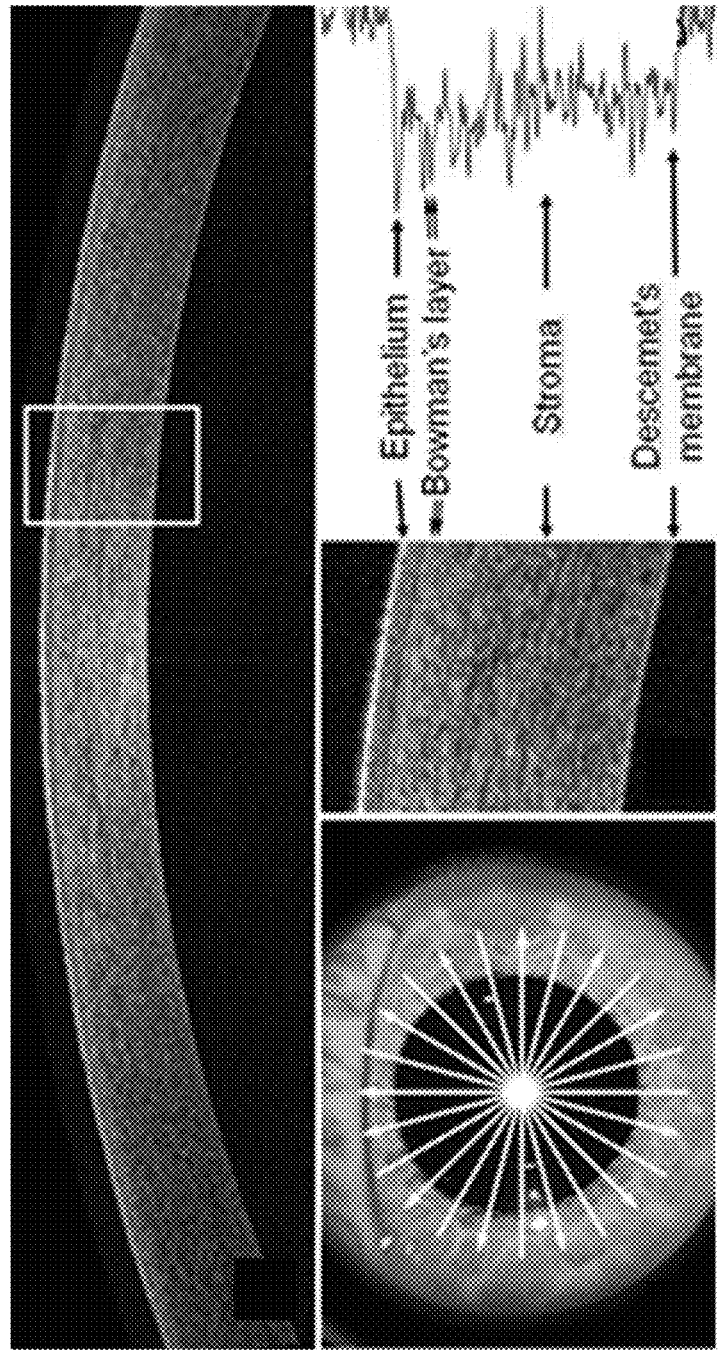
FIGS. 7A-7D illustrate an OCT (e.g., Avanti XR OCT) scan pattern to map epithelial thickness, pachymetry and corneal topographies, in accordance with various embodiments.

Two OCT systems may be used in this Example (see Table 2). The RTVue-XR Avanti (Optovue, Inc., Fremont, Calif.) is an FDA-approved spectral-domain OCT system that may serve as the primary instrument for this Example. A higher-speed swept-source OCT (SS-OCT) system may be used for assessing whether faster scan speed improve the repeatability and diagnostic accuracy of OCT-based corneal parameters. Both systems comply with the American National Standard for safe ocular exposure to lasers and are being used in ongoing IRB-approved clinical studies. The corneal mapping diameter will be 9 mm for the Avanti (see FIGS. 7) and 10 mm for the SS-OCT prototype. Because the SS-OCT beam can be scanned more quickly without losing signal strength, the B-frame rate (200 images/sec) is 3 times higher than the Avanti despite the A-line scan rate (speed) being only 1.4 times higher. Furthermore, SS-OCT can achieve greater imaging depth to include the iris so that pupil centration can be obtained by OCT image post-processing. Pupil centration of Avanti corneal maps may be provided by post-processing of video frames (see FIG. 7). Both systems have sufficient resolution to measure the epithelial thickness.

TABLE 2

Specifications of Fourier-Domain OCT Systems in This Study

| Manufacturer/ Name | Speed (Hz) | $\lambda$ (nm) | Depth Resolution ($\mu$m) | Scan Depth (mm) | Scan Width (mm) |
|---|---|---|---|---|---|
| Optovue/ Avanti | 70,000 | 840 | 5 | 2.4 | 9 |
| Custom/ SS-OCT | 100,000 | 1050 | 7 | 4.3 | 20 |

Abbreviation:
swept-source OCT (SS-OCT).
Speed in axial lines per second, $\lambda$ = central wavelength, full-width-half-maximum depth and scan depth are specified in tissue.

Approach—OCT Scanning Procedure and Image Processing

The OCT scans may be obtained with the subject's head stabilized in a chin rest and gaze fixed on an internal target. The OCT scan may be centered on the pupil using a real-time video display. Scans acquisition may start a predetermined time (e.g., 2 seconds) after a blink to standardize the tear film condition. Raw OCT data may be exported. Custom software may be used to identify corneal boundaries, remove distortion due to index transition ('dewarping'), register and average repeated OCT images acquired at the same location, and locate the epithelium-Bowman's layer interface. The anterior and posterior corneal surfaces may be corrected for fan distortions due to scan optics. Zernike analysis may be performed on the reconstructed surface, and all Zernike terms higher than $8^{th}$ order ($Z_8^8$) may be discarded to obtain a smooth surface.

Approach—Corneal Topography Procedure and Processing

Corneal topography may be obtained by the Topolyzer Placido-disc topography system (Alcon, Inc.) and the Pentacam Scheimpflug tomography system. For each eye, four consecutive measurements may be obtained to test for measurement repeatability. The Zernike analysis from the Topolyzer may be exported for the planning of topography-guided PTK.

The keratoconus percentage index (KISA %) may be calculated based on the exported axial power maps from the Pentacam. A KISA % index greater than 100 may be considered keratoconus and less than 60 may be considered normal. In addition to the KISA % index, a number of parameters (e.g., 26 basic parameters) may be exported from Pentacam. For example, the exported parameters may include 19 parameters for the anterior surface, 4 for pachymetry, 2 for the posterior surface, and 1 for the anterior segment. Advanced keratoconus parameters will also be exported including Belin-Ambrosio's display D value (BAD-D), index of surface variance (ISV), and index of height asymmetry (IHA).

Approach: Develop OCT-Based Classification System of Corneal Shape Irregularities.

Conventional corneal topography can miss FFK because early anterior topographic steepening is masked by focal epithelial thinning. It also cannot distinguish ectasia from other conditions that could also cause focal steepening (see Table 3). Thus there is a need to use OCT to provide more sensitive detection of FFK as well as other corneal shape irregularities and distinguish them from each other.

Preliminary Results on Keratoconus Diagnosis Based on OCT Corneal Epithelial and Pachymetry Maps Keratoconus typically produces inferotemporal thinning of the cornea and epithelium. As discussed above, diagnostic parameters based on OCT corneal pachymetry and epithelial thickness maps may be used to detect this characteristic pattern, based on 6-mm corneal maps from a 26-kHz spectral OCT. It has been determined that the Epithelial PSD (also referred to as Epi-PSD) is the most accurate parameter at differentiating keratoconus from normal eyes. The Epi-PSD may be calculated by the root-mean-square of the pattern deviation map, defined as percent deviation of epithelial thickness from the normal reference from a group of healthy subjects. The diagnostic sensitivity and specificity were both 100% when tested in 76 normal and 35 keratoconic eyes. In another study of 50 subclinical (CDVA 20/20 or better) keratoconus and 50 normal control eyes, the sensitivity was 96% at 100% specificity. Epi-PSD is also a very sensitive parameter for detecting uneven epithelium in all corneal shape irregularities.

Therefore, Epi-PSD may be used as the primary diagnostic parameter to detect all four classes of corneal irregularities listed in Table 3. Once abnormality is detected, ectasias will be distinguished from other conditions using posterior topography and pachymetry parameters, in accordance with the global consensus definition of keratoconus and ectasia as a process that include both focal thinning and posterior steepening.

TABLE 3

Comprehensive OCT Classification System of Corneal Shape Irregularities

| Cause of Irregularity | Anterior Topography | Epithelial Thickness | Pachymetry | Posterior Topography | Examples |
|---|---|---|---|---|---|
| Ectasia | Inferior Steepening | Inferior Thinning | Inferior Thinning | Inferior Steepening | Keratoconus, PMD, post-LASIK ectasia |
| Epithelial Deformation | Steepening Depression | Thickening Thinning | Normal Normal | Normal Normal | Warpage, EBMD, dry eye, epitheliopathy |
| Stromal Addition or Subtraction | Steepening Depression | Thinning Thickening | Thickening Thinning | Normal/depr. Normal/steep. | LASIK, PRK, scar, Salzmann, ulcer, stromal dystrophies, corneal inlay |
| Stromal Distortion | Steepening Depression | Thinning Thickening | Normal/thin Normal | Steepening Depression | PK, RK, AK |

Abbreviations:
pellucid marginal degeneration (PMD),
contact lens-related corneal warpage (warpage),
epithelial basement membrane dystrophy (EBMD),
photorefractive keratectomy (PRK),
Salzmann's nodular degeneration (Salzmann),
penetrating keratoplasty (PK),
radial keratotomy (RK),
astigmatic keratotomy (AK).

OCT Parameters for Classification of Corneal Shape Irregularities

OCT is the only type of corneal topography-tomography system that has sufficient depth resolution to map epithelial thickness. The high resolution also enables more accurate pachymetry. As described herein, anterior and posterior mean curvature maps may also be used as a more accurate way to detect topographic steepening and flattening. Four novel composite indices to combine information from the OCT maps (Table 4) are provided as follows:

Ectasia Index. While many conditions could cause focal steepening of the anterior corneal surface, keratoconus and other ectasias are unique in causing both posterior steepening and stromal thinning. The Ectasia Index captures this characteristic combination by fitting the focal steepening of the posterior topography and pachymetry with two-dimensional Gaussian waveforms as previously described.

Coincident-Thinning (CT) Index. Another unique feature of ectasias is the coincident pachymetric and epithelial thinning. This pattern is captured by the Coincident-Thinning (CT) index, which is a multiplication of the magnitudes of fitted Gaussian waveforms of pachymetry and epithelial thickness.

Epithelium-Anterior Topography (EAT) Index (also referred to herein as the Warpage Index). In conditions caused by primary epithelial deformations (e.g., contact-lens related corneal warpage), focal epithelial thinning is coincident with focal anterior topographic depression. In contrast, in diseases where the epithelium compensates for anterior stromal contour changes (e.g., keratoconus, LASIK), focal epithelial thinning is coincident with focal anterior topographic steepening (see FIG. 6). The contrast between these two patterns is brought out by the Warpage Index (EAT Index), which is calculated by the covariance of the epithelial and anterior topography maps.

Pachymetry-Anterior Topography (PAT) Index. Corneal stromal addition or subtraction (e.g. LASIK) produce coincident focal anterior steepening or flattening with pachymetric thickening or thinning, respectively. This is captured by the covariance of pachymetry and the anterior topography.

TABLE 4

OCT-Based Composite Indices for Classifying Corneal Shape Irregularities

| Index | Anterior Mean Curvature* | Epithelial Thickness* | Pachymetry* | Posterior Mean Curvature* |
|---|---|---|---|---|
| Ectasia Index | — | — | Gaussian | Gaussian |
| Coincident-Thinning (CT) Index | — | Gaussian | Gaussian | — |
| Epithelium-Anterior Topography (EAT) Index | Covariance | Covariance | — | — |
| Pachymetry-Anterior Topography (PAT) Index | Covariance | — | Covariance | — |

*All maps are first converted to pattern deviation maps (% deviation from the average pattern of the normal group).
In the Gaussian operation, the maps are convolved with a 3-mm full-width half-maximum 2-dimensional Gaussian waveform, then values at the center of the ectasia from 2 maps are multiplied to measure ectasia severity. The center of ectasia is identified as the minimum location on the Gaussian filtered pachymetry map.
The covariance is the average product of the deviations of two maps from their respective means. All indices have as unit % deviation from normal.

As previously discussed, the Epi-PSD, Ectasia Index and the Warpage Index (also referred to as the EAT Index) to analyze 15 normal eyes, 45 keratoconic eyes, 8 FFK eyes, and 11 eyes with contact lens-related corneal warpage. All of the keratoconic eyes, 88% of FFK eyes, and 82% of warpage eyes had abnormally high Epi-PSD, while all normal eyes had normal values (100% specificity). The Ectasia Index and Warpage Index together correctly differentiated all keratoconus eyes and most FFK eyes from warpage eyes, with the exception of 2 contact lens-wearing FFK eyes in which the warpage predominated (see FIG. 2). In that example embodiment, topography from a Placido-disc system was used. However, in other embodiments, image processing software may be used to measure both anterior and posterior topography using both OCT systems described above in conjunction with Example 2.

In various embodiments, a decision tree (e.g., the 4-level decision tree as shown in FIG. 8) may be used to carry out the comprehensive classification process. We tested the comprehensive corneal irregularity classification system using a simple human-built 4-level tree outlined (FIG. 5). The preliminary results (see Table 5) show that 96.1% of 77 abnormal eyes were detected by Epi-PSD. Of the detected abnormal eyes, classification was correct in 100% of 45 keratoconus eyes, 71% of 7 FFK eyes (100% for 3 FFK with no contact lenses and 50% for 4 FFK wearing hard contact lenses), 100% of 9 warpage eyes, 67% of 3 dry eyes, 80% of 5 granular dystrophy and 100% of 2 post-PK eyes.

L, et al. Dysfunctional tear syndrome: a Delphi approach to treatment recommendations. Cornea. September 2006; 25(8):900-907 and/or Lin H, Yiu S C. Dry eye disease: A review of diagnostic approaches and treatments. *Saudi J Ophthalmol.* July 2014; 28(3):173-181, incorporated by reference herein), or epithelial basement membrane dystrophy (EBMD, n=54, defined by negative fluorescein staining and intra/subepithelial opacity in map, dot, or fingerprint distribution). These eyes must have asymmetry documented by an ISV value larger than 37 or irregularity documented by an IHA value larger than 19 on Pentacam topography.

1C. Stromal addition or subtraction (n=60): Patients may be tested who have corneal scar, Salzmann's degeneration, stromal dystrophies, and complicated (visual complaints) LASIK/PRK.

TABLE 5

Statistical Power Analysis and Sample Size Calculation for Irregularity Classification

| | | Preliminary Data | | | Target | | |
|---|---|---|---|---|---|---|---|
| Class | Group | Preliminary Data (N) | Detecting Abnormality | Classification Accuracy | Target Accuracy | 95% CI of Accuracy | Sample size* |
| Normal | Normal | 15 | 0% | 100% | NA | | |
| Ectasia | Keratoconus (non-FFK) | 45 | 100% | 100% | NA | | |
| | FFK | 8 | 88% | 71% | 80% | (68%~89%) | 60 |
| Epithelial Deformation | EBMD | 3 | 100% | 100% | 80% | (73%~86%) | 54 |
| | Dry Eye | 3 | 100% | 67% | 80% | | 54 |
| | CL-Related Warpage | 11 | 82% | 100% | 80% | | 54 |
| Stromal Addition/Subtraction (dystrophy) | | 5 | 100% | 80% | 80% | (68%~89%) | 60 |
| Stromal Distortion (PK) | | 2 | 100% | 100% | 80% | (68%~89%) | 60 |

Abbreviations: forme fruste keratoconus (FFK), contact lenses (CL), epithelial basement membrane dystrophy (EBMD), confidence interval (CI), penetrating keratoplasty (PK).
*Statistical power = 0.8. EBMD, dry eye, CL-related warpage will be grouped for classification.
Keratoconus (non-FFK) can already be identified with 100% accuracy and therefore improvement on that is not a goal.

Cross-Sectional Study of OCT-Based Comprehensive Classification of Corneal Shape Irregularities The comprehensive OCT-based classification system may be used to identify four causes of corneal irregularities (see Table 3). The classification system may detect keratoconus, particularly FFK that is often missed by a conventional topography-based index (KISA %), and may differentiate it from the other three causes of corneal irregularities. For example, the classification process may diagnose subjects' eyes within the following groups:

1A. Keratoconus (n=250). The study may include Keratoconus patients with corrected distance visual acuity (CDVA) 20/25 in the better eyes. Both eyes of each participant are examined. Based on previous study experience, ~25% of participants (60) should have FFK, defined as the better eye of asymmetric keratoconus (KISA %>100 in the worse eye and KISA %<100 in the better eye). Thus defined and based on the knowledge that keratoconus is a bilateral disease, FFK is generally considered the best challenge to test new methods to detect previously undetectable keratoconus.

1B. Epithelial deformation (n=162). Patients may be tested who have contact lens corneal warpage (n=54), dry eye (n=54, defined by fluorescein staining [Oxford scale I] (e.g., as described in Bron A J, Evans V E, Smith J A. Grading of corneal and conjunctival staining in the context of other dry eye tests. Cornea. October 2003; 22(7):640-650, incorporated by reference herein) due to aqueous deficiency [Schirmer test ≤5 mm] or evaporative [tear breakup time ≤5 sec] dry eye, e.g., as described in Behrens A, Doyle J J, Stern 1D. Stromal distortion (n=60). Patients with complicated radial keratotomy and corneal transplants may be tested.

1E. Normal control (n=160). Subjects with healthy eyes and no previous surgery may be tested. Data from randomly selected 100 healthy participants may be used to establish the normal population average maps. The remaining 60 healthy subjects may be used for the corneal shape irregularity classification study.

Rigor: Primary statistical analysis and sample size The primary goal of this study is to test if OCT indices (see FIG. 9) can correctly detect corneal shape irregularities and then classify the underlying corneal conditions. The sample sizes noted above are calculated to be sufficient to establish classification accuracy to within ±12% of target (see Table 5).

The classification accuracy may be evaluated using the decision tree used to generate the preliminary results (e.g., as shown in FIG. 8). To further improve performance, machine learning may be used to build a higher level decision tree that incorporate more OCT diagnostic parameters (see FIG. 9). For example, additional OCT diagnostic parameters that may be used in some embodiments are described in Li Y, Chamberlain W, Tan O, Brass R, Weiss J L, Huang D. Subclinical keratoconus detection by pattern analysis of corneal and epithelial thickness maps with optical coherence tomography. *J Cataract Refract Surg.* February 2016; 42(2):284-295; Li Y, Meisler D M, Tang M, et al. Keratoconus diagnosis with optical coherence tomography pachymetry mapping. *Ophthalmology.* December 2008; 115 (12):2159-2166; and Tang M, Shekhar R, Miranda D, Huang D. Characteristics of keratoconus and pellucid marginal degeneration in mean curvature maps. *Am J Ophthalmol*. December 2005; 140(6):993-1001, incorporated by reference herein). The Random Forests algorithm (e.g., as described in (Alickovic E, Subasi A. Medical Decision Support System for Diagnosis of Heart Arrhythmia using DWT and Random Forests Classifier. *J Med Syst*. April 2016; 40(4):108 and/or Yang F, Wang H Z, Mi H, Lin C D, Cai W W. Using random forest for reliable classification and cost-sensitive learning for medical diagnosis. *BMC Bioinformatics*. Jan. 30, 2009; 10 Suppl 1:S22, incorporated by reference herein) may be used because it is able to reduce over-training of deep decision trees by averaging trees trained using different subsets of the data. The resulting screening tool offers better performance than the current standard keratoconus screening tool in the clinic. To demonstrated, the detection sensitivity of FFK using the OCT indices may be compared with that obtained by the Pentacam BAD-D parameter. For classification performance, a second Random Forests algorithm using Pentacam parameters (e.g., as described in Ruiz Hidalgo I, Rodriguez P, Rozema J J, et al. Evaluation of a Machine-Learning Classifier for Keratoconus Detection Based on Scheimpflug Tomography. *Cornea. June* 2016; 35(6):827-832, incorporated by reference herein) may be used and its accuracy may be compared with that of the OCT-based algorithm.

A secondary goal is to use the OCT indices as measures of disease severity. The repeatability of the OCT indices may be evaluated by intraclass correlation. Correlation with disease severity (high/low-contrast CDVA, quality of vision) may be assessed by Spearman rho (or Pearson's R if appropriate). Quality of vision may be evaluated using NEI Visual Function Questionnaire 25 (VFQ-25, see, e.g., Zadnik K, Barr J T, Edrington T B, et al. Corneal scarring and vision in keratoconus: a baseline report from the Collaborative Longitudinal Evaluation of Keratoconus (CLEK) Study. *Cornea. November* 2000; 19(6):804-812, incorporated by reference herein). For dry eyes, disease severity measures may also include a fluorescein staining score, Schirmer's test, and tear breakup time. For keratoconus, maximum and steep-meridian keratometry ($K_{max}$ and $K_{steep}$) may be used as reference severity measures (see, e.g., Szalai E, Berta A, Hassan Z, Modis L, Jr. Reliability and repeatability of swept-source Fourier-domain optical coherence tomography and Scheimpflug imaging in keratoconus. *J Cataract Refract Surg*. March 2012; 38(3):485-494; and/or Hashemi H, Yekta A, Khabazkhoob M. Effect of keratoconus grades on repeatability of keratometry readings: Comparison of 5 devices. *J Cataract Refract Surg*. May 2015; 41(5):1065-1072).

Example 3

The methods described in the present disclosure may be implemented in an integrated system that is fully automated or assembled from different components that may require some manual intervention. In general, a system according to the present disclosure may comprise the components of a corneal topography measuring device capable of measuring and generating a corneal topography and an optical coherence tomography device, wherein both devices a capable of producing data in digital format or in a format that can be digitized, and a processing unit. The corneal topography measuring device may include, but not be limited to, Placido-ring topography, slit-scan corneal topography, Shiempflug-camera corneal tomography, raster photogrammetry, optical coherence tomography, or any other suitable cornea measuring devices known in the art. The processing unit may be a personal computer, a workstation, an embedded processor, or any other suitable data processing device commonly known in the art.

In addition to being implemented in a system, the methods of the present disclosure may also be provided in the form of software encoded on a computer readable medium for distribution to end users. Example computer media may include, but not be limited to, floppy disks, CD-roms, DVDs, hard drive disks, flash memory cards, downloadable files on an internet accessible server, or any other computer readable media commonly known in the art.

Figure 10:
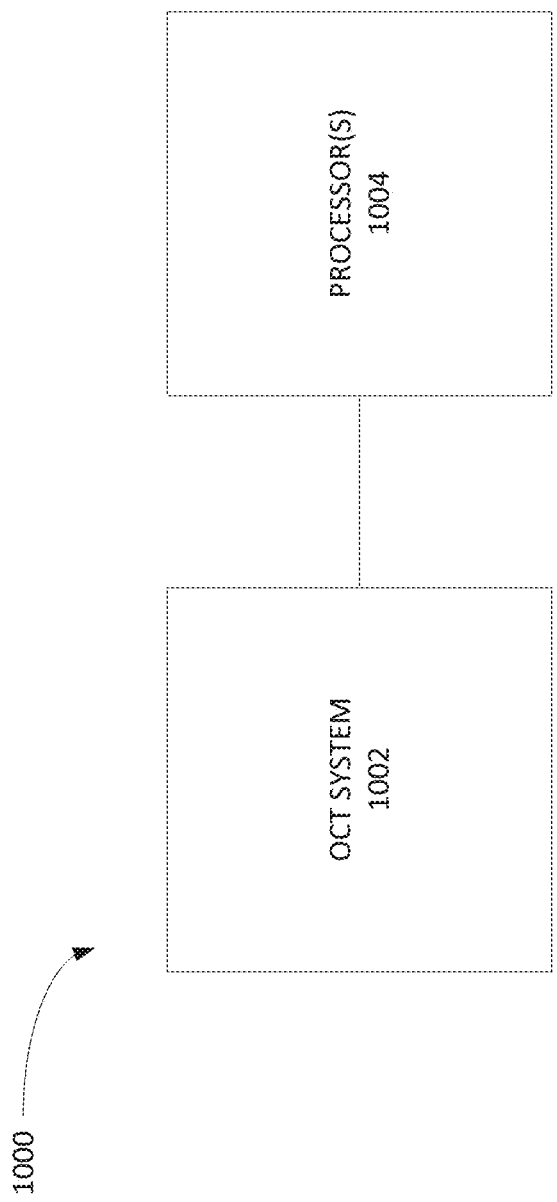
FIG. 10 is a schematic of an example system for corneal classification in accordance with the disclosure.

FIG. 10 schematically shows an example system 1000 for OCT image processing in accordance with various embodiments. System 1000 comprises an OCT system 1002 configured to acquire an OCT image comprising OCT interferograms and one or more processors or computing systems 1004 that are configured to implement the various processing routines described herein. OCT system 1000 can comprise an OCT system suitable for OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods depicted in FIG. 4 and/or FIG. 8 described above, can be implemented as a computer application, computer service, computer API, computer library, and/or other computer program product.

Figure 11:
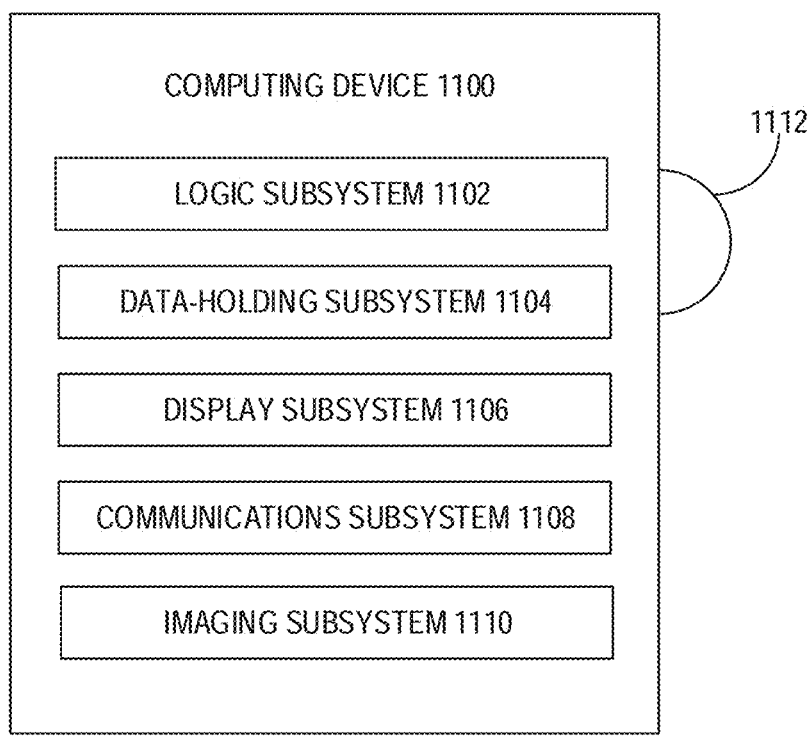
FIG. 11 is a schematic of an example computing system in accordance with the disclosure.

FIG. 11 schematically shows a non-limiting computing device 1100 that can perform one or more of the methods and processes described herein. For example, computing device 1100 can represent a processor included in system 2000 or system 1000 described above, and can be operatively coupled to, in communication with, or included in an OCT system or OCT image acquisition apparatus. Computing device 1100 is shown in simplified form. It is to be understood that virtually any computer architecture can be used without departing from the scope of this disclosure. In different embodiments, computing device 1100 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1100 includes a logic subsystem 1102 and a data-holding subsystem 1104. Computing device 1100 can optionally include a display subsystem 1106, a communication subsystem 1108, an imaging subsystem 1110, and/ or other components not shown in FIG. 11. Computing device 1100 can also optionally include user input devices such as manually actuated buttons, switches, keyboards, mice, game controllers, cameras, microphones, and/or touch screens, for example.

Logic subsystem 1102 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1104 can include one or more physical, non-transitory, devices configured to hold data and/or instructions executable by the logic subsystem to implement the herein described methods and processes. When such methods and processes are implemented, the state of data-holding subsystem 1104 can be transformed (e.g., to hold different data).

Data-holding subsystem 1104 can include removable media and/or built-in devices. Data-holding subsystem 1104 can include optical memory devices (e.g., CD, DVD, HD-DVD, Blu-Ray Disc, etc.) semiconductor memory devices (e.g., RAM, EPROM, EEPROM, etc.) and/or magnetic memory devices (e.g., hard disk drive, floppy disk drive, tape drive, MRAM, etc.) among others. Data-holding subsystem 1104 can include devices with one or more of the following characteristics: volatile, nonvolatile, dynamic, static, read/write, read-only, random access, sequential access, location addressable, file addressable, and content addressable. In some embodiments, logic subsystem 1102 and data-holding subsystem 1104 can be integrated into one or more common devices, such as an application specific integrated circuit or a system on a chip.

FIG. 11 also shows an aspect of the data-holding subsystem in the form of removable computer-readable storage media 1112, which can be used to store and/or transfer data and/or instructions executable to implement the herein described methods and processes. Removable computer-readable storage media 1112 can take the form of CDs, DVDs, HD-DVDs, Blu-Ray Discs, EEPROMs, flash memory cards, USB storage devices, and/or floppy disks, among others.

When included, display subsystem 1106 can be used to present a visual representation of data held by data-holding subsystem 1104. As the herein described methods and processes change the data held by the data-holding subsystem, and thus transform the state of the data-holding subsystem, the state of display subsystem 1106 can likewise be transformed to visually represent changes in the underlying data. Display subsystem 1106 can include one or more display devices utilizing virtually any type of technology. Such display devices can be combined with logic subsystem 1102 and/or data-holding subsystem 1104 in a shared enclosure, or such display devices can be peripheral display devices.

When included, communication subsystem 1108 can be configured to communicatively couple computing device 1100 with one or more other computing devices. Communication subsystem 1108 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1100 to send and/or receive messages to and/or from other devices via a network such as the Internet.

When included, imaging subsystem 1110 can be used acquire and/or process any suitable image data from various sensors or imaging devices in communication with computing device 1100. For example, imaging subsystem 1110 can be configured to acquire OCT image data, e.g., interferograms, as part of an OCT system, e.g., OCT system 1002 described above. Imaging subsystem 1110 can be combined with logic subsystem 1102 and/or data-holding subsystem 1104 in a shared enclosure, or such imaging subsystems can comprise periphery imaging devices. Data received from the imaging subsystem can be held by data-holding subsystem 1104 and/or removable computer-readable storage media 1112, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computer-based method of classifying corneal shape abnormalities, the method comprising:
    combining data from at least two of the following corneal maps of a cornea: a topography map, a pachymetry map, and an epithelial thickness map—to obtain one or more indices of corresponding distortion; and
    distinguishing between at least two corneal shape abnormalities in the cornea based on the one or more indices of corresponding distortion.

2. The method of claim 1, wherein the topography map, the epithelial thickness map, and the pachymetry map are pattern deviation (PD) maps.

3. The method of claim 2, wherein combining the data from the at least two corneal maps includes fitting a function on a first one of the corneal maps to obtain a first fitted function and fitting the function on a second one of the corneal maps to obtain a second fitted function; and
    combining the first and second fitted functions.

4. The method of claim 3, wherein the function is a Gaussian function.

5. The method of claim 4, wherein the first fitted function and the second fitted function are combined via multiplication.

6. The method of claim 1, wherein the combining the data from the at least two corneal maps includes determining a covariance between a first one of the corneal maps and a second one of the corneal maps.

7. The method of claim 1, wherein the one or more indices of corresponding distortion includes an ectasia index obtained by combining data from the topography map and the pachymetry map.

8. The method of claim 1, wherein the one or more indices of corresponding distortion includes a coincident-thinning index obtained by combining data from the pachymetry map and the epithelial thickness map.

9. The method of claim 1, wherein the one or more indices of corresponding distortion includes a warpage index obtained by combining data from the topography map and the epithelial thickness map.

10. The method of claim 1, wherein the topography map is a mean curvature map of an anterior surface of the cornea.

11. The method of claim 1, wherein the topography map is a mean curvature map of the posterior surface of the cornea.

12. The method of claim 1, wherein one or more of the topography map, the pachymetry map, or the epithelial thickness map are obtained using optical coherence tomography.

13. A computer-based method of classifying corneal shape abnormalities, the method comprising:
obtaining an epithelial thickness map of a cornea;
obtaining a pachymetry map of the cornea;
determining a coincident-thinning (CT) index based on the epithelial thickness map and the pachymetry map; and
classifying the cornea based on the CT index to differentiate an ectatic condition of the cornea from a non-ectatic condition of the cornea.

14. The method of claim 13, wherein the epithelial thickness map and the pachymetry map are pattern deviation (PD) maps.

15. The method of claim 14, wherein determining the CT index includes:
fitting a function on the epithelial thickness map and the pachymetry map to generate a fitted epithelial function and a fitted pachymetry function; and
combining the fitted epithelial function and the fitted pachymetry function.

16. The method of claim 15, wherein the function is a Gaussian function, and wherein the fitted epithelial function and the fitted pachymetry function are combined via multiplication.

17. The method of claim 13, further comprising:
obtaining a topography map of the subject's cornea; and
determining warpage index based on the topography map and the epithelial thickness map;
wherein the cornea is classified further based on the warpage index.

18. The method of claim 17, wherein the topography map is a mean curvature map of an anterior surface of the cornea.

19. The method of claim 13, further comprising:
determining an epithelial thickness pattern standard deviation (PSD) value based on the epithelial thickness map;
wherein the cornea is classified further based on the epithelial thickness PSD value.

20. The method of claim 13, further comprising:
obtaining an anterior topography map of the subject's cornea; and
determining a pachymetry anterior topography (PAT) index based on the anterior topography map and the pachymetry map;
wherein the cornea is classified further based on the PAT index.

21. The method of claim 20, wherein the PAT index is determined based on a covariance between the topography map and the pachymetry map.

22. A computer-based method of classifying corneal shape abnormalities, the method comprising:
obtaining a posterior topography map of a cornea;
obtaining a pachymetry map of the cornea;
determining an ectasia index based on the posterior topography map and the pachymetry map; and
classifying the cornea based on the ectasia index as having one or more than one corneal shape abnormality existing together.

23. The method of claim 22, wherein the topography map and the pachymetry map are pattern deviation (PD) maps.

24. The method of claim 23, wherein determining the ectasia index includes:
fitting a function on the posterior topography map and the pachymetry map to generate a fitted topography function and a fitted pachymetry function; and
combining the fitted topography function and the fitted pachymetry function.

25. The method of claim 24, wherein the function is a Gaussian function, and wherein the fitted topography function and the fitted pachymetry function are combined via multiplication.

26. The method of claim 22, wherein the posterior topography map is a mean curvature map of a posterior surface of the cornea.

27. The method of claim 22, further comprising:
obtaining an anterior topography map of the cornea;
obtaining an epithelial thickness map of the cornea; and
determining warpage index based on the epithelial thickness map and the anterior topography map;
wherein the cornea is classified further based on the warpage index.

28. The method of claim 27, further comprising:
determining an epithelial thickness pattern standard deviation (PSD) value based on the epithelial thickness map;
wherein the cornea is classified further based on the epithelial thickness PSD value.

29. The method of claim 1, wherein distinguishing between at least two corneal shape abnormalities in the cornea further comprises differentiating between an ectasia, epithelial deformation, and non-ectatic stromal changes.

30. The method of claim 9, wherein a positive value of the warpage index indicates corneal warpage, while a negative value of the warpage index indicates keratoconus.

31. The method of claim 20, wherein a value of the CT index greater than a CT threshold indicates ectasia, while the value of the CT index less than the CT threshold indicates non-ectatic stromal changes based on the PAT index.

32. The method of claim 22, wherein a value of the ectasia index below an ectasia threshold indicates an epithelial deformation of the cornea, while the value of the ectasia index above the ectasia threshold indicates co-existence of both keratoconus and warpage of the cornea.

33. The method of claim 32, wherein the epithelial deformation of the cornea further includes pure warpage erosion, or deposits.

34. The method of claim 28, wherein a combination of the epithelial thickness PSD, warpage index, and ectasia index form a tripartite classification system on the basis of which normal, warpage, and ectasia conditions of the cornea are differentiated among each other.

* * * * *